(12) United States Patent
Itoh et al.

(10) Patent No.: US 9,090,896 B2
(45) Date of Patent: Jul. 28, 2015

(54) MOLECULE CAPABLE OF BINDING TO ADRENOCORTICOTROPIC HORMONE, AND USE THEREOF

(71) Applicant: SYSMEX CORPORATION, Kobe-shi, Hyogo (JP)

(72) Inventors: Katsunori Itoh, Kobe (JP); Hiroyuki Kabata, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

(21) Appl. No.: 14/316,343

(22) Filed: Jun. 26, 2014

(65) Prior Publication Data

US 2014/0322821 A1     Oct. 30, 2014

Related U.S. Application Data

(63) Continuation of application No. PCT/JP2012/083097, filed on Dec. 20, 2012.

(30) Foreign Application Priority Data

Dec. 28, 2011   (JP) ................................. 2011-289028

(51) Int. Cl.
| | |
|---|---|
| *C07H 21/02* | (2006.01) |
| *C07H 21/04* | (2006.01) |
| *C12Q 1/68* | (2006.01) |
| *C12N 15/115* | (2010.01) |
| *C07K 14/695* | (2006.01) |
| *G01N 21/78* | (2006.01) |
| *G01N 33/74* | (2006.01) |
| *C07K 14/575* | (2006.01) |
| *G01N 21/64* | (2006.01) |
| *G01N 21/76* | (2006.01) |

(52) U.S. Cl.
CPC ............ *C12N 15/115* (2013.01); *C07K 14/575* (2013.01); *C07K 14/695* (2013.01); *C12Q 1/6811* (2013.01); *G01N 21/78* (2013.01); *G01N 33/74* (2013.01); *C12N 2310/16* (2013.01); *C12Q 2525/117* (2013.01); *C12Q 2525/205* (2013.01); *G01N 21/6428* (2013.01); *G01N 21/76* (2013.01); *G01N 2333/695* (2013.01)

(58) Field of Classification Search
CPC ........... C12Q 1/6811; C12Q 2525/117; C12Q 2525/205; C12N 15/115; G01N 21/6428
USPC ......................... 536/23.1, 24.3; 435/6.1, 6.17
See application file for complete search history.

(56) References Cited

FOREIGN PATENT DOCUMENTS

| WO | 03/078623 A1 | 9/2003 |
|---|---|---|
| WO | 2009/012410 A1 | 1/2009 |
| WO | 2009/028345 A1 | 3/2009 |
| WO | 2009/043491 A1 | 4/2009 |
| WO | 2011/142798 A2 | 11/2011 |

OTHER PUBLICATIONS

International Search Report for PCT/JP2012/083097 dated Feb. 12, 2013.

*Primary Examiner* — Jezia Riley
(74) *Attorney, Agent, or Firm* — Sughrue Mion, PLLC

(57) ABSTRACT

The present invention relates to a molecule capable of binding to adrenocorticotropic hormone (ACTH) with high affinity. The present invention also relates to use of the molecule for detection and/or purification of ACTH.

14 Claims, 13 Drawing Sheets

MOLECULE CAPABLE OF BINDING TO ADRENOCORTICOTROPIC HORMONE, AND USE THEREOF

CROSS-REFERENCE TO RELATED APPLICATION

This application is a continuation of International Application PCT/JP2012/083097 filed on Dec. 20, 2012, which claims benefit of Japanese patent application JP 2011-289028 filed on Dec. 28, 2011, both of which are incorporated herein by reference in their entireties.

BACKGROUND OF THE INVENTION

The present invention relates to a molecule capable of binding to adrenocorticotropic hormone (ACTH) with high affinity. The present invention also relates to use of the molecule for detection and/or purification of ACTH.

Among various peptides contained in blood, some peptides show varied blood concentration in certain pathological conditions from normal conditions. Such peptides are attracting attention as disease markers in the field of clinical tests. For example, for clinical tests of Simmonds disease and Sheehan's syndrome resulting from reduction in secretion of pituitary hormones, kits for ACTH detection are used which utilize antigen-antibody reaction.

However, preparation of antibodies which are used for antigen-antibody reaction is extremely complicated and quality control of antibodies is also difficult.

Alternative to the methods utilizing antigen-antibody reaction, new peptide detection methods, i.e., detection methods utilizing aptamers which are nucleic acid molecules specifically binding to target peptides have been recently developed. For example, WO 2003/078623 discloses a method for producing an aptamer which is capable of binding to a target protein with high affinity and contains a modified nucleotide.

SUMMARY OF THE INVENTION

Although aptamers capable of specifically recognizing various proteins or polypeptides have been developed in the art, molecules capable of binding to ACTH with high affinity have not been discovered.

Thus the present invention provides an ACTH-binding molecule including a nucleic acid sequence having a modified base represented by any one of (a), (b) and (c):

(a) $X_1TTX_2X_3TX_3TX_4GX_4GAX_5TX_2X_1TX_6C$ (b) $AX_5X_7GTX_2X_6CX_3TX_4GTX_2X_3TX_6CTX_8$ (c) $X_6CTX_2AX_5TX_2X_9AX_1TX_7GX_6CAX_5TX_2$ wherein $X_1$ to $X_9$ respectively represent modified bases represented by the following formulae, wherein P represents a phosphate group:

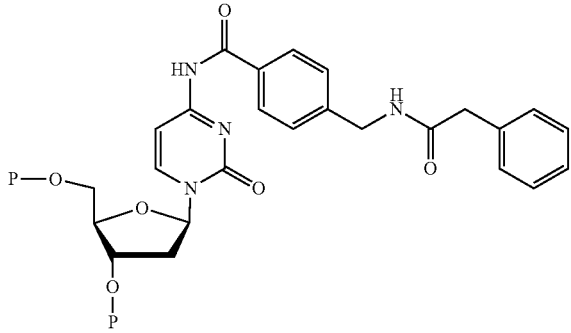

X<sub>5</sub>

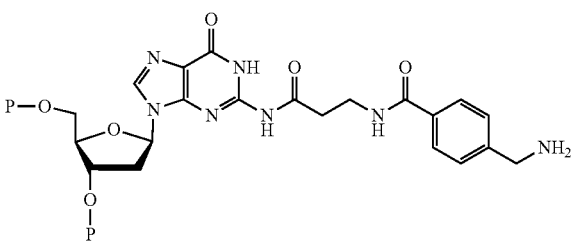

X<sub>6</sub>

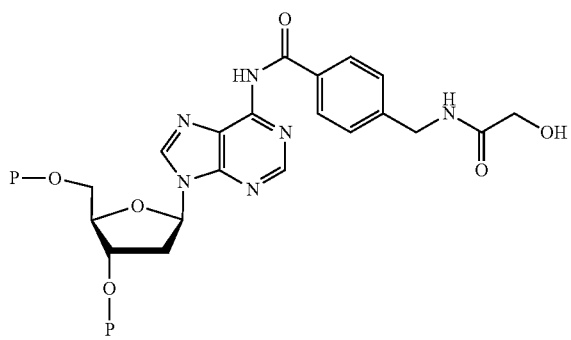

X<sub>7</sub>

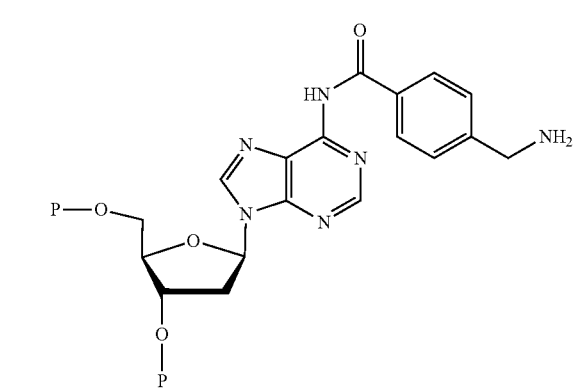

X<sub>8</sub>

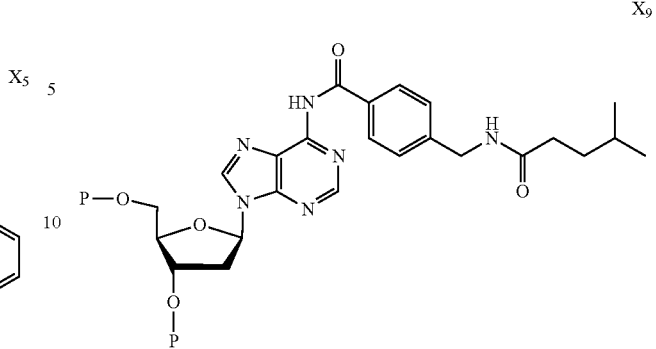

X<sub>9</sub>

The present invention also provides methods for detecting and purifying ACTH by using the ACTH-binding molecule or a carrier linked to the molecule.

DETAILED DESCRIPTION OF THE EMBODIMENTS

[1] ACTH-Binding Molecule

Figure 1A:
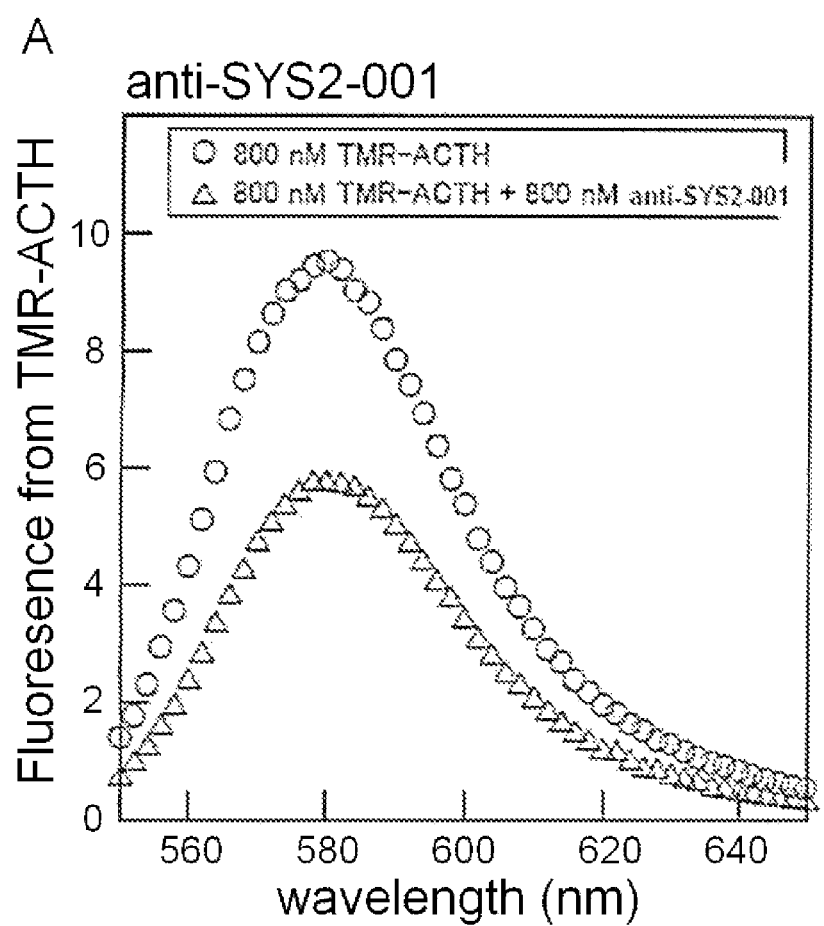
FIGS. 1A, 1B and 1C show fluorescence spectra of a sample solution containing an ACTH peptide and sample solutions containing the ACTH peptide and ACTH-binding molecules of the present invention.

The term "ACTH-binding molecule" as used herein means a functional molecule having affinity towards ACTH and capable of specifically binding to ACTH.

The ACTH-binding molecule of the present invention has a nucleic acid sequence containing a modified base represented by any one of (a), (b) and (c) above and has affinity towards ACTH.

ACTH is a hormone consisting of 39 amino acids, secreted from the pituitary gland and acts on adrenal cortex to promote secretion of corticosteroid.

In the embodiments of the present invention, ACTH may be natural ACTH produced in vivo, a peptide produced by cells such as mammalian cells, insect cells and E. coli cells to which a gene encoding ACTH has been introduced or a chemically synthesized peptide. Amino acid sequences of ACTH have high homology among organisms and thus ACTH may be derived from any organisms producing ACTH without limitation, which may include mammals (e.g., human, mouse, rat, canine, rabbit), avian (e.g., ostrich), fish (e.g., dogfish) and the like.

In the embodiments of the present invention, ACTH targeted by the ACTH-binding molecule may be a full-length peptide or a fragment thereof. The fragment is preferably a peptide consisting of at least amino acids positions 1 to 24 of ACTH.

The modified base contained in the ACTH-binding molecule of the present invention is a base containing a substituent on an amino group of adenine, guanine and cytosine in a nucleoside (or nucleotide). The substituent may be introduced by any well known methods in the art without limitation, which may include the methods represented by the following schemes:

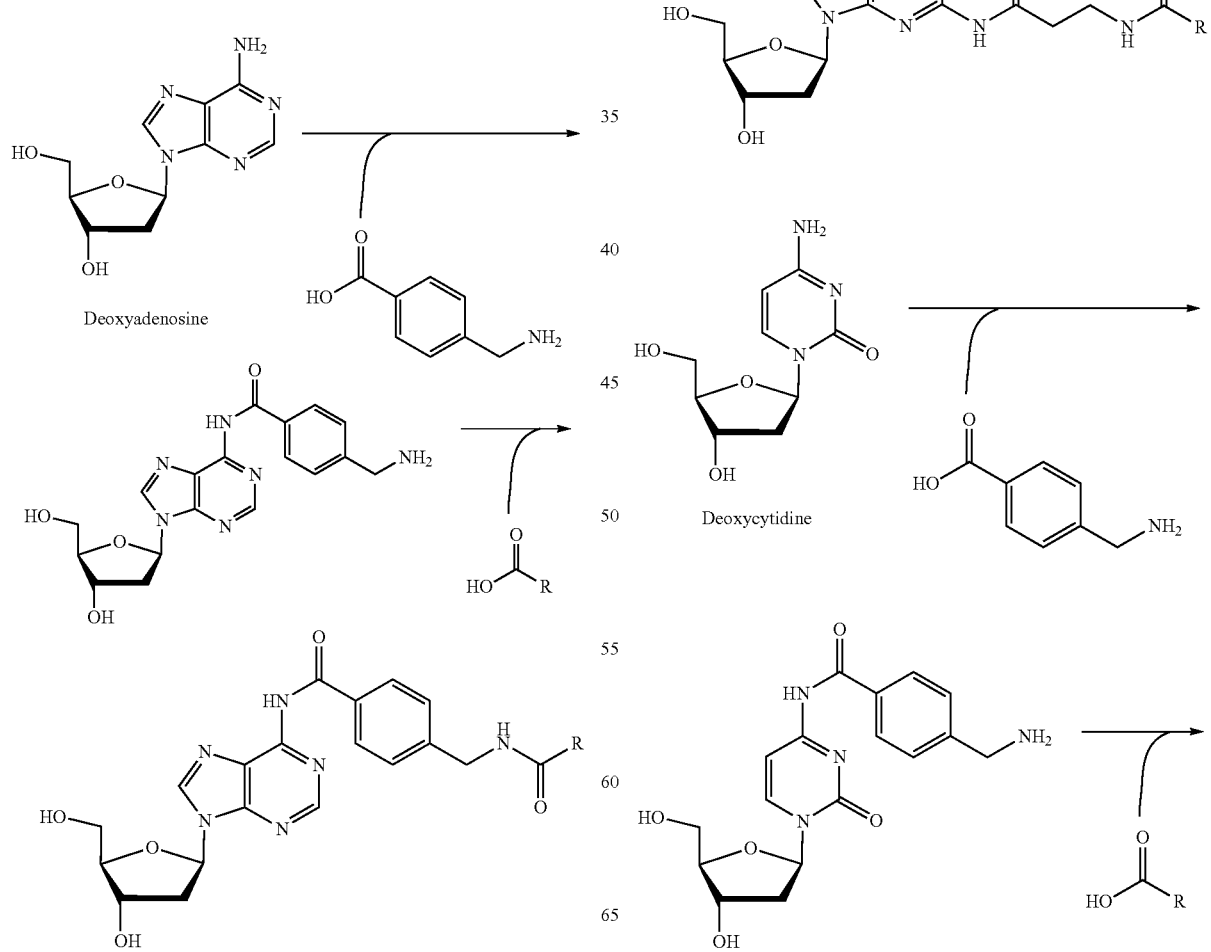

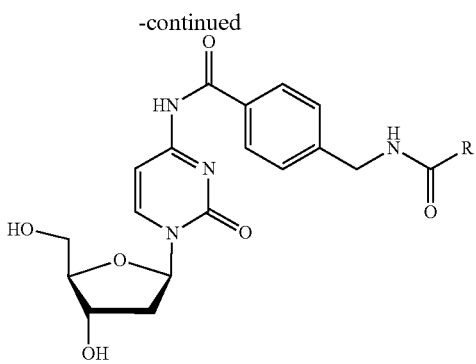

In the above schemes, R is a group represented by any of —(CH$_2$)$_3$COOH, —CH$_2$CH$_2$CH(CH$_3$)$_2$, —CH$_2$OH, —CHNH$_2$CH$_2$NH$_2$ and the following formulae (1) to (4):

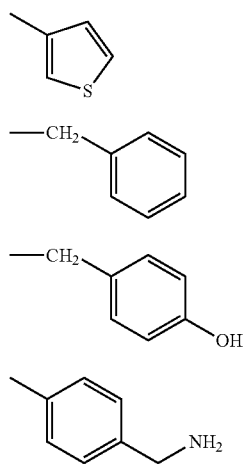

In the embodiments of the present invention, the ACTH-binding molecule can be produced by synthesizing a polynucleotide containing nucleosides having the modified base and a normal base. The synthesis method is not particularly limited and may be a well known method in the art. Such a method may include, for example, the phosphoramidite method, the diester method, the triester method, the phosphite method, the thiophosphite method, the H-phosphonate method and the like. The synthesis may be carried out on a commercially available automated DNA synthesizer.

In the embodiments of the present invention, the ACTH-binding molecule may be a DNA or a RNA. Thus the nucleic acid sequence of the ACTH-binding molecule of the present invention also encompasses a molecule having the sequence containing uracil (U) instead of thymine (T).

In the embodiments of the present invention, the ACTH-binding molecule may have any structure without limitation as far as it does not interfere with the binding to ACTH and preferably has a linear structure.

In the embodiments of the present invention, the ACTH-binding molecule may have an additional sequence. Namely the ACTH-binding molecule may have such an additional sequence on one or both ends of the nucleic acid sequence represented by any one of (a), (b) and (c). The additional sequence is not particularly limited as far as it does not interfere with the binding of the ACTH-binding molecule to ACTH and may be, for example, a nucleic acid sequence for amplifying the ACTH-binding molecule by PCR or a nucleic acid sequence for stabilizing the structure of the ACTH-binding molecule. The nucleic acid sequence for amplifying the ACTH-binding molecule may be appropriately selected according to the sequence of primers to be used. The nucleic acid sequence for stabilizing the structure of the ACTH-binding molecule may be, for example, a sequence which can form an intramolecular complementary base pair of 15 to 35 bases when attached to both ends of the nucleic acid sequence represented by any one of (a), (b) and (c).

The additional sequence may have any length without limitation and may generally be 100-mer or less and preferably 80-mer or less. The additional sequence may be added during synthesis of the polynucleotide having the nucleic acid sequence represented by any one of (a), (b) and (c).

In the embodiments of the present invention, the ACTH-binding molecule may have a linker. Namely the ACTH-binding molecule may have such a linker on one or both ends of the nucleic acid sequence represented by any one of (a), (b) and (c). The linker is not particularly limited as far as it does not interfere with the binding of the ACTH-binding molecule to ACTH and may preferably be a linker for attaching the ACTH-binding molecule to a carrier. The linker may preferably be a linear molecule such as linear synthesized polymers and linear natural polymers. Because static interaction contributes to the binding between the ACTH-binding substance and ACTH, the polymer is preferably a nonionic polymer which does not inhibit the binding of the ACTH-binding substance to ACTH.

The linear synthesized polymer may include, for example, alkyl groups having 1 to 700 carbon atoms, polyethylene glycols, polyvinyl alcohols (including partially saponified polyvinyl acetates), polyvinyl methyl ether, poly-2-hydroxyethyl methacrylate, polyvinylpyrrolidones, polymers of acrylamide or acrylamide derivatives, polyvinylacetamides and polyvinylformamides and the like. Among these, polyethylene glycols are preferred because they have high hydrophilicity and are readily available and synthesized. Polyvinylpyrrolidones and polyvinylacetamides are preferred because they rarely inhibit the binding between the ACTH-binding substance and ACTH.

The linear natural polymer may include, for example, nucleic acids, polysaccharides and proteins such as hydrophilic polypeptides. The linker may be added to the ACTH-binding molecule according to a well known method.

In the embodiments of the present invention, the ACTH-binding molecule may be linked to a well known carrier and used. Thus a carrier linked to the ACTH-binding molecule of the present invention is also encompassed by the scope of the present invention.

The carrier may be of, for example, polysaccharides, plastics, glass and the like. The carrier may have a shape of, for example, beads, gel and the like. Specific examples of the carrier may include Sephallose beads, agarose beads, magnetic beads, glass beads, silicone gel and the like. The carrier may be packed in a column before use. The carrier may be a multi-well plate, a substrate for microarray and the like.

The ACTH-binding molecule and the carrier may be directly linked or indirectly linked through another substance such as the linker described above. The ACTH-binding molecule may be linked to the carrier according to a well known method in the art. For example, the ACTH-binding molecule and the carrier may be linked through binding of biotin to avidin or streptavidin by adding biotin to the ACTH-binding molecule of the present invention and adding avidin or streptavidin to the carrier.

The carrier linked to the ACTH-binding molecule of the present invention can be used as, for example, a biosensor for detecting and/or purifying ACTH in a sample.

Because the ACTH-binding molecule of the present invention can bind to ACTH with high affinity, the ACTH-binding molecule and the carrier linked thereto can be used as a reagent for ACTH detection in the embodiments of the present invention. When the ACTH-binding molecule of the present invention is used as the detection reagent, the ACTH-binding molecule may be labeled with a well known labeling substance in the art such as enzymes, dyes, fluorescent substances and radioisotopes. The ACTH-binding molecule labeled with the substance and a sample suspected to contain ACTH may be mixed and then ACTH which bound to the ACTH-binding molecule may be detected based on the signal originating from the label.

In another embodiment of the present invention, the ACTH-binding molecule and the carrier linked thereto of the present invention can be used as a pharmaceutical agent for prophylaxis and therapy of diseases which may involve hypersecretion of ACTH or as an ACTH inhibitor. When the ACTH-binding molecule is used as the agent or reagent, the ACTH-binding molecule may be dissolved in water, saline or an appropriate buffer to obtain a solution having a suitable concentration, which solution may be administered to a subject via a suitable route or may be added to a culture medium of living cells.

[2] Methods for Detection and Purification of ACTH

The present invention provides a method for detection and a method for purification of ACTH in a sample by using the ACTH-binding molecule.

The method for detecting ACTH of the present invention includes the step of mixing a sample with the ACTH-binding molecule or the carrier linked thereto of the present invention and the step of analyzing binding of the ACTH-binding molecule to ACTH in the mixture obtained in the previous step, thereby detecting ACTH.

In the embodiments of the present invention, the sample is not particularly limited as far as it is suspected to contain ACTH and is preferably a fluid sample which is suspected to contain ACTH. The sample may be a biological sample. The biological sample may include, for example, blood, plasma, serum, body fluid and the like. The sample may be mixed with the ACTH-binding molecule or the carrier linked thereto of the present invention under any condition without limitation and a person skilled in the art can appropriately select the condition. When the sample is a fluid sample for example, the amount of the ACTH-binding molecule added may be, in terms of the final concentration, 1 to 500 nM and preferably 5 to 100 nM. The mixing may be carried out under the temperature and duration of about 20 to 37° C. and 30 seconds to 5 minutes.

In a preferred embodiment of the present invention, binding of the ACTH-binding molecule to ACTH may be analyzed by irradiating the mixture obtained in the step of mixing with light to obtain optical information. The optical information may include a wavelength of reflected light, a fluorescence intensity, an absorbance and the like.

When the optical information which is the wavelength of reflected light is obtained, the mixture is irradiated with white light and the variation in the wavelength of reflected light is measured over time by Reflectometric Interference Spectroscopy (RIfS). RIfS is a method for detecting intermolecular interaction by injecting a sample into a flow path on a substrate to allow interaction of molecules on the substrate and irradiating with white light to measure interfering effect of reflected light from the substrate as an amount of wavelength variation.

When the optical information which is the wavelength of reflected light is obtained, another preferable method may be the one utilizing the principle of Surface Plasmon Resonance (SPR). The method utilizing the principle of SPR is a method in which a substrate onto which a molecule and the like are immobilized is irradiated with light having a specific wavelength on the surface devoid of a flow path (namely the surface where a molecule and the like are not immobilized) so as to obtain total reflection and detect the resulting reflected light and variation in the reflected angle of reflected light is analyzed to measure variation in the amount of substances immobilized on the substrate. For example, ACTH may be injected into a flow path on a substrate onto which the ACTH-binding molecule has been immobilized, the surface devoid of the flow path is irradiated with light having a specific wavelength so as to obtain total reflection and detect reflected light and the reflected angle of the reflected light is detected, so that the variation in mass due to binding of the ACTH-binding molecule to ACTH may be detected.

When the optical information which is the fluorescence intensity is obtained, the ACTH-binding molecule of the present invention which has been labeled with a well known fluorescent substance may be used. A mixture of the labeled ACTH-binding molecule and the sample is irradiated with light capable of exciting the labeling fluorescent substance, a signal derived from the label is obtained and thus ACTH bound to the ACTH-binding molecule can be detected.

When the optical information which is the absorbance is obtained, it is preferable to use chemiluminescence using chemiluminescence enzymes such as peroxidases. The method using chemiluminescence may be similar to the ELISA (Enzyme-Linked ImmunoSorbent Assay) method. For example, ACTH is allowed to bind on a substrate onto which the ACTH-binding molecule has been immobilized followed by enzyme labeling and enzyme reaction to convert a chromogenic substrate into a pigment. By analyzing the absorbance obtained by measuring the extent of the pigment on a chromometer, ACTH bound to the ACTH-binding molecule may be detected.

By using the binding molecule of the present invention, ACTH can be detected easily in short time with decreased cost compared to the detection utilizing antigen-antibody reaction.

The method for purifying ACTH of the present invention includes the step of mixing a sample with the ACTH-binding molecule or the carrier linked thereto of the present invention and the step of obtaining a complex of the ACTH-binding molecule linked to the carrier and ACTH from the mixture obtained in the previous step.

The step of mixing the sample and the carrier in the method of purifying is the same as the step described for the method for detecting ACTH of the present invention.

The complex of the ACTH-binding molecule linked to the carrier and ACTH may be obtained from the mixture by any means without limitation. For example, when the sample is fluid and the carrier is beads, the complex of the ACTH-binding molecule linked to the carrier and ACTH may be obtained by centrifugation. Alternatively, the complex of ACTH in a sample and the ACTH-binding molecule linked to the carrier may be obtained by passing the sample through a column in which the carrier linked to the ACTH-binding molecule of the present invention is packed.

The method for releasing ACTH from the complex is well known in the art. For example, ACTH may be released from the complex by adding to the complex a solution having high salt concentration.

By using the binding molecule of the present invention, ACTH can be purified easily in short time with decreased cost compared to the purification utilizing antigen-antibody reaction.

The present invention is more specifically described hereinafter by way of Examples which do not limit the present invention.

EXAMPLES

Example 1

Preparation of ACTH-Binding Molecule (1-1) ACTH Peptide

An ACTH peptide used which was a target of the ACTH-binding molecule was a synthesized peptide by adding to the N-terminal of a peptide consisting of amino acids positions 1 to 24 of ACTH a linker "Biotin-PEG4-DDDDK-" (produced by Biologica Co.). In the linker, "DDDDK" is an amino acid sequence which is a cleavage site by enterokinase and "Biotin-PEG4" is a tag for immobilizing the peptide onto a resin used for affinity chromatography described hereinbelow.

(1-2) Screening of ACTH-Binding Molecule

Screening of the ACTH-binding molecule was carried out according to the SELEX (Systematic Evolution of Ligands by EXponential enrichment) method. Nucleosides containing 9 different modified bases were synthesized by substituting amino groups in adenine, guanine and cytosine according to the following schemes:

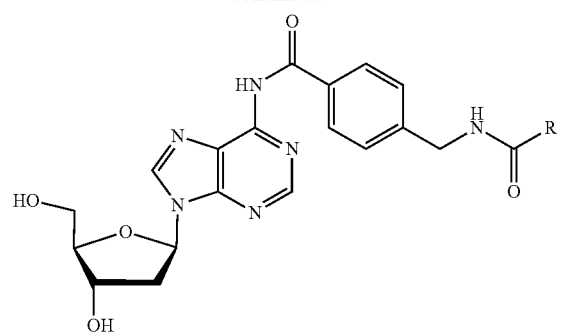
Deoxyadenosine

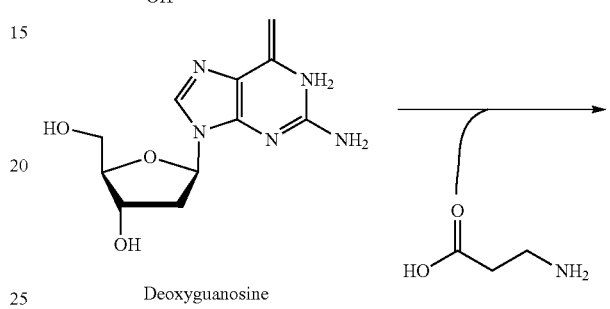

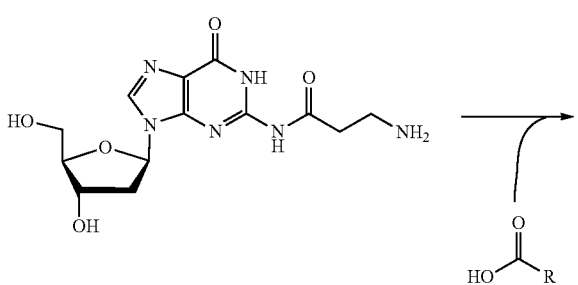
Deoxyguanosine

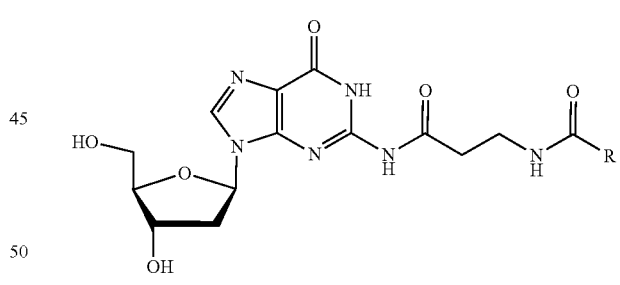

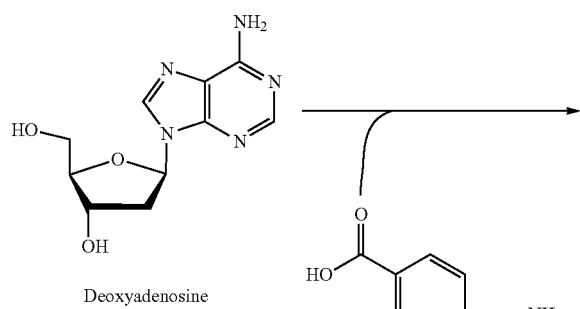

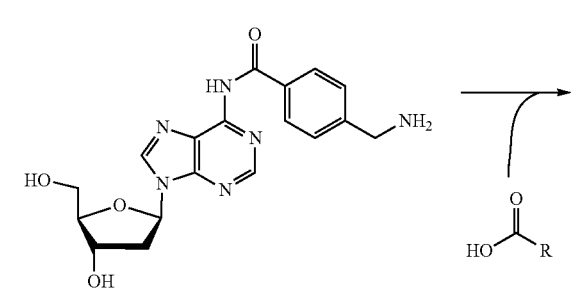
Deoxycytidine

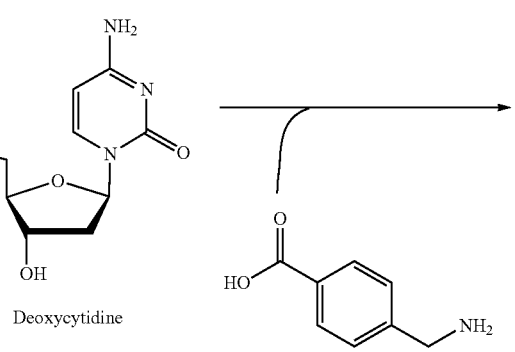

-continued

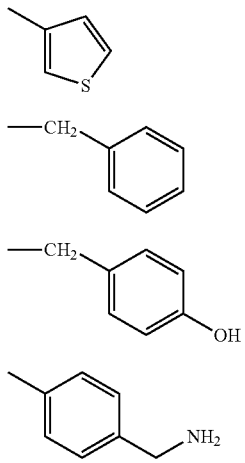

In the above schemes, R is a group represented by any of —(CH$_2$)$_3$COOH, —CH$_2$CH$_2$CH(CH$_3$)$_2$, —CH$_2$OH, —CHNH$_2$CH$_2$NH$_2$ and the following formulae (1) to (4):

By using nucleosides including the obtained modified nucleosides on an automated DNA synthesizer, a random library containing oligonucleotides of constant sequence 1 (35-mer: SEQ ID NO: 1)-random oligonucleotide sequence (20-mer)-constant sequence 2 (33-mer: SEQ ID NO: 2). The constant sequences 1 and 2 had the following sequences:

```
Constant sequence 1:
GAAGGTGAAG GTCGGCTGAA GCATTAGACC TAAGC

Constant sequence 2:
GCTTAGGTCT AATGCACCAT CATCACCATC TTC
```

Then a resin to which the ACTH peptide synthesized in (1-1) was immobilized was used to carry out affinity chromatography on the random library. As a result, 75 ACTH-binding molecule candidates were obtained. The candidates were subjected to primary screening according to the SPR (surface plasmon resonance) method which resulted in 12 ACTH-binding molecule candidates having high affinity towards the ACTH peptide. The 12 candidates were subjected to secondary screening according to fluorescence titration to obtain 3 ACTH-binding molecules having high affinity towards the ACTH peptide. The obtained ACTH-binding molecules are respectively designated as anti-SYS2-001, anti-SYS2-002 and anti-SYS2-021. The sequences of the ACTH-binding molecules are as follows:

```
anti-SYS2-001: X₁TTX₂X₃TX₃TX₄GX₄GAX₅TX₂X₁TX₆C anti-SYS2-002: AX₅X₇GTX₂X₆CX₃TX₄GTX₂X₃TX₆CTX₈ anti-SYS2-021: X₆CTX₂AX₅TX₂X₉AX₁TX₇GX₆CAX₅TX₂
``` wherein $X_1$ to $X_9$ respectively represent modified bases represented by the following formulae, wherein P represents a phosphate group:

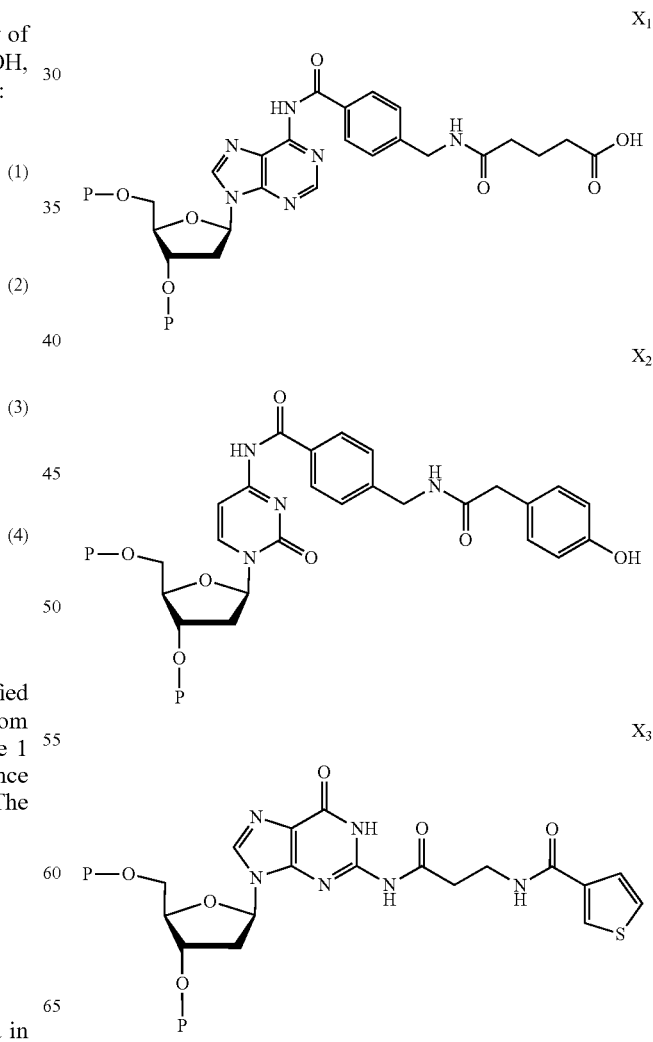

X₄

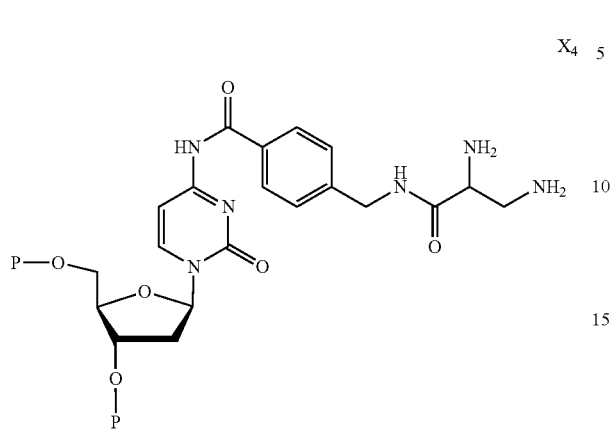

X₅

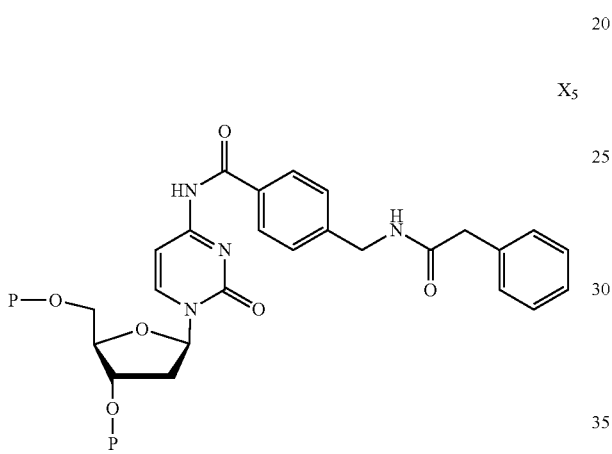

X₆

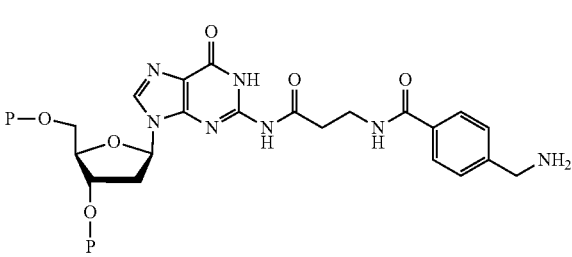

X₇

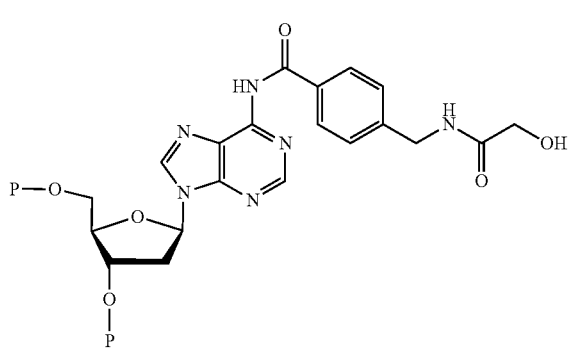

X₈

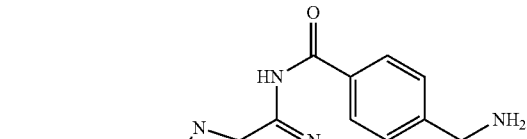

X₉

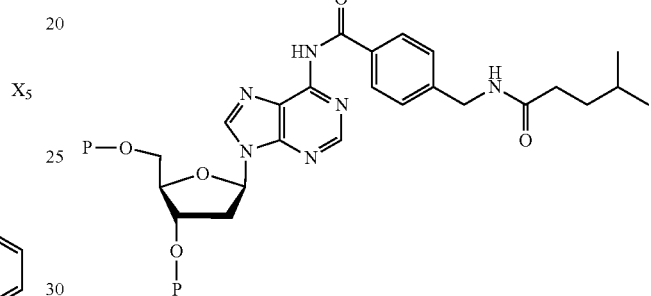

Example 2

Detection of Binding of ACTH-Binding Molecule to ACTH Peptide and Calculation of Dissociation Equilibrium Constant (KD)

(2-1) Fluorescent Labeled ACTH Peptide

An ACTH peptide used which was a target of the ACTH-binding molecule was a TMR-ACTH peptide obtained by labeling a peptide consisting of amino acids positions 1 to 24 of ACTH with a red fluorescent dye, tetramethylrhodamine (TMR) (produced by Biologica Co.).

(2-2) Fluorescence Spectra Measurement and Measurement Based on Fluorescence Titration The TMR-ACTH peptide synthesized in (2-1) was dissolved in 0.5× Tris buffered saline (TBS) (20 mM Tris-HCl (pH 7.4), 150 mM NaCl) to the final concentration of 800 nM to obtain a sample solution A. The anti-SYS2-001 obtained in Example 1 and the TMR-ACTH peptide were dissolved in 0.5×TBS to the final concentrations respectively of 1600 nM and 800 nM to obtain a sample solution B. The anti-SYS2-002 and anti-SYS2-021 were also dissolved in 0.5×TBS with the TMR-ACTH peptide similarly to the sample solution B to obtain sample solutions C and D.

Figure 1B:
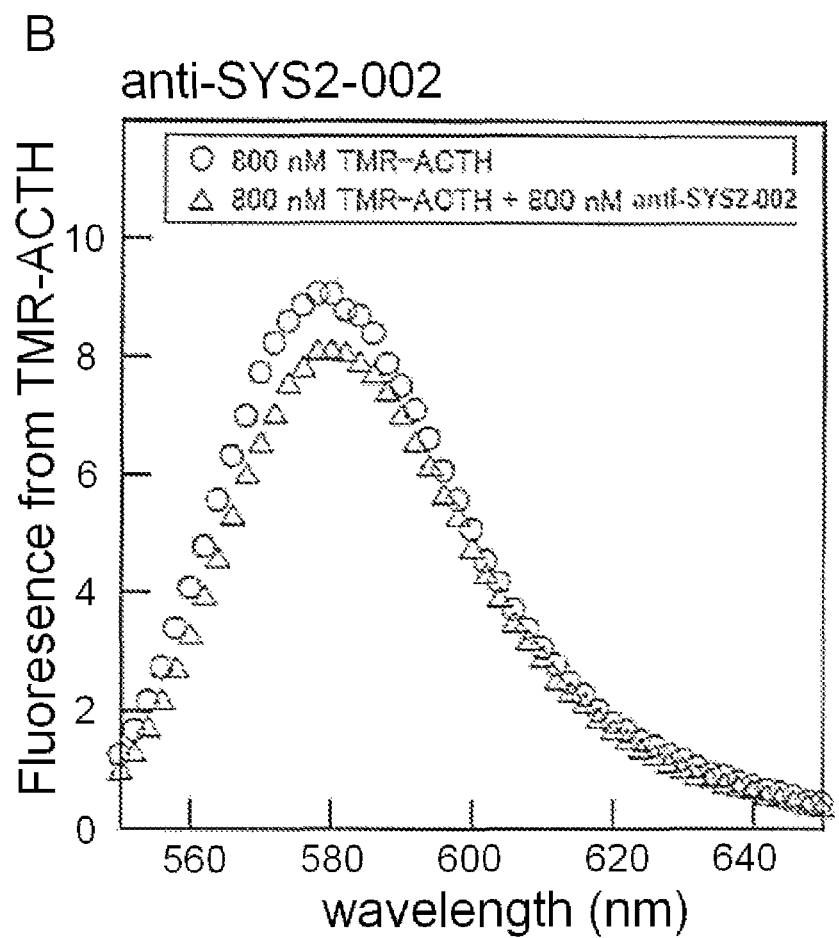
Figure 1C:
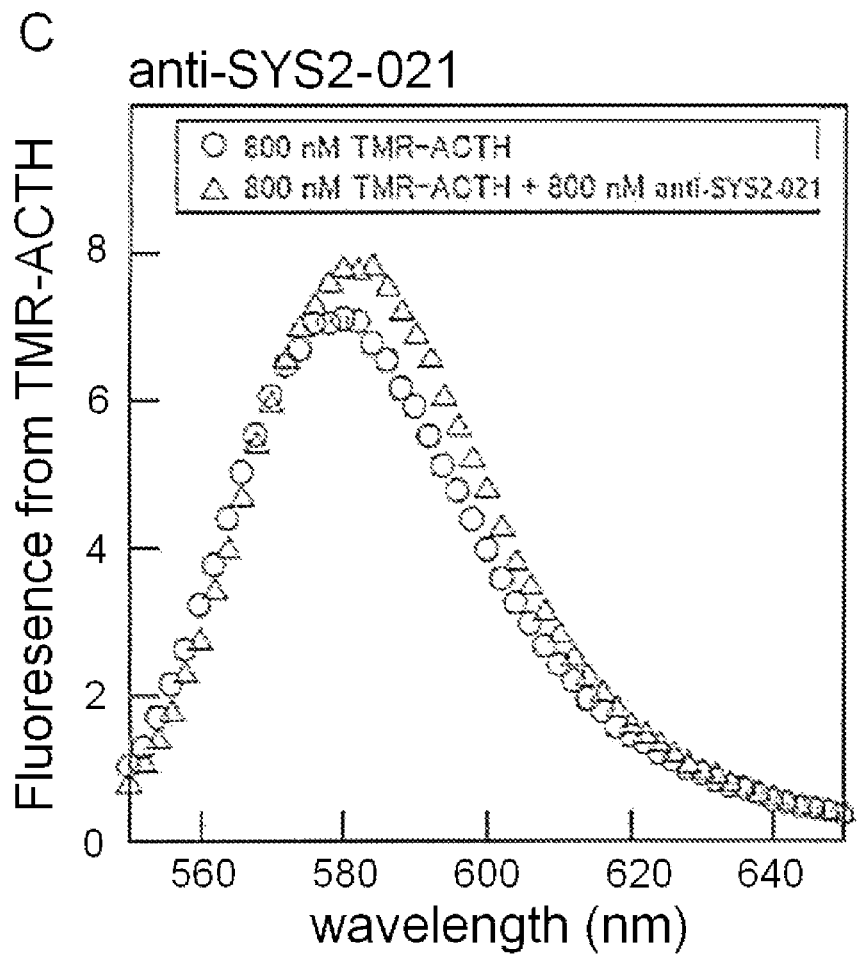

The sample solutions A to D were respectively measured for fluorescence spectra at exciting wavelength of 540 nm and fluorescence wavelength of 550 to 650 nm on Hitachi Fluorescence Spectrophotometer F-7000 (FL) (Hitachi High-Technologies Corporation). The obtained fluorescence spectra are shown in FIGS. 1A, 1B and 1C.

Figure 2A:
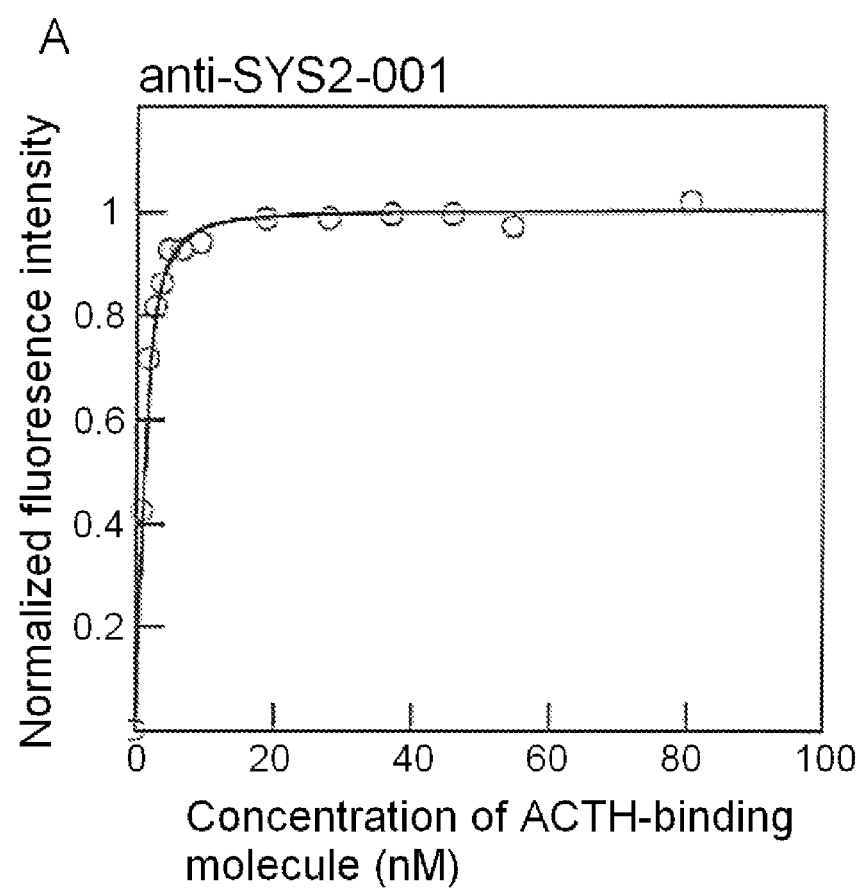
FIGS. 2A, 2B and 2C are graphs obtained by plotting data obtained from samples with the concentration of an ACTH-binding molecule on the X axis and the normalized fluorescence intensity on the Y axis.
Figure 2B:
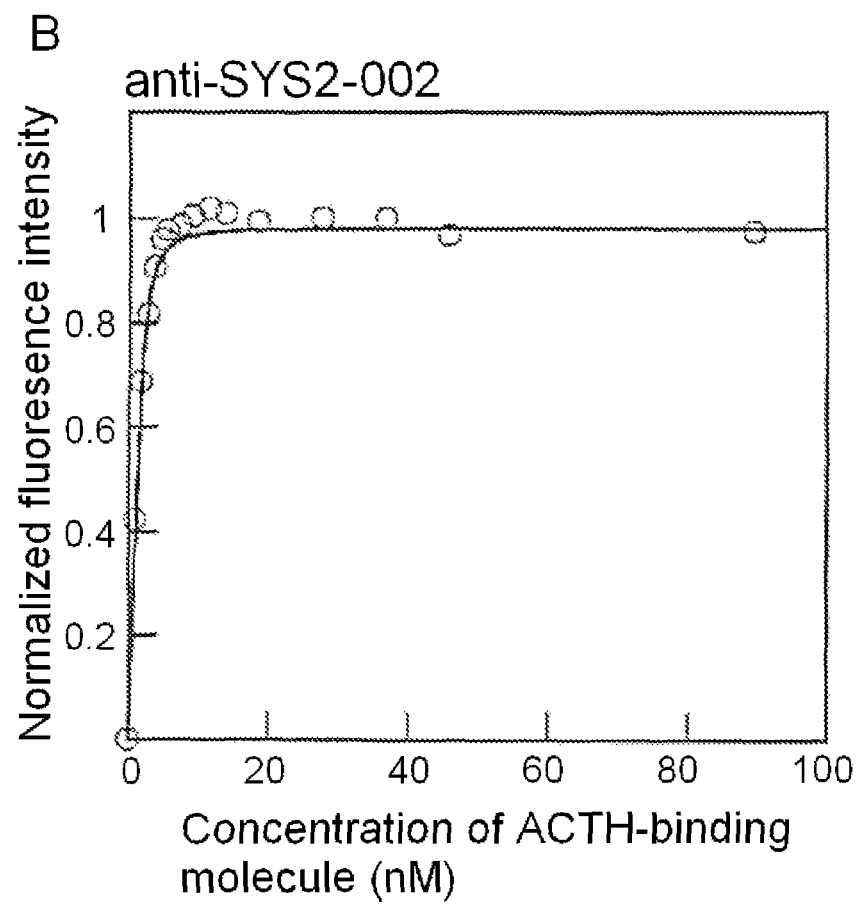
Figure 2C:
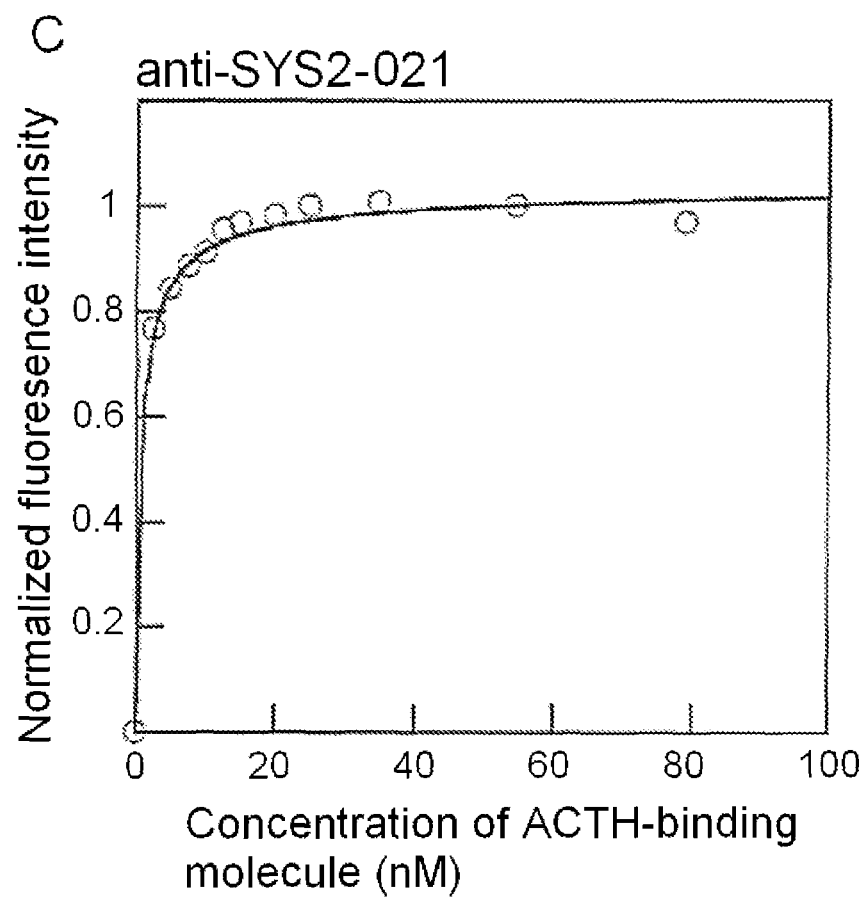

The sample solutions B, C and D are respectively mixed with the sample solution A to adjust the concentration of the ACTH-binding molecule to 0 to 800 nM. The obtained solutions were measured for fluorescence intensity at an excitation wavelength of 540 nm and fluorescence wavelength of 580 nm. The obtained fluorescence intensity was normalized and the data for the solutions were plotted on coordinates with the concentration (nM) of the ACTH-binding molecule on the X axis and the normalized fluorescence intensity on the Y axis. Curve fitting of the obtained graph to the following formula (I) by KaleidaGraph (Hulinks Inc.) allowed calculation of the KD value of binding between the ACTH-binding molecule and the ACTH peptide. The analysis results are shown in FIGS. 2A, 2B and 2C.

$$Y = a \times X^b / (X^b + K_D^b)$$ Formula (I)

(wherein in the formula (I), a represents a constant and b represents Hill coefficient).

It is found from FIGS. 1A, 1B and 1C that the fluorescence of the TMR-ACTH peptide was quenched by addition of the ACTH-binding molecules. Thus it is believed that the TMR-ACTH peptide is bound to the ACTH-binding molecules of the present invention.

It is found from FIGS. 2A, 2B and 2C that the KD values indicting the affinity of binding of the ACTH-binding molecule to the TMR-ACTH peptide are $1.1 \times 10^{-9}$ M for anti-SYS2-001, $1.1 \times 10^{-9}$ M for anti-SYS2-002 and $6.1 \times 10^{-10}$ M for anti-SYS2-021. The aptamer disclosed in WO 2003/078623 has the KD value of $1.0 \times 10^{-7}$ to $1.0 \times 10^{-9}$ M, and thus it is found that the ACTH-binding molecules of the present invention have affinity towards the ACTH peptide at or higher than that of the aptamer of the conventional art.

Example 3

Detection of Binding and Dissociation of ACTH-Binding Molecule and ACTH Peptide by Reflectometric Interference Spectroscopy (RIfS)

(3-1) Peptide

An ACTH peptide used was a peptide consisting of amino acids positions 1 to 24 of ACTH (produced by Biologica Co.). Among the peptides identified as disease markers in Villanueva J, et al. (J din Invest 116(1), p. 271-284, 2006), peptides having about 25 amino acid residues and an isoelectric point in acidic (pI value of less than 5.5), neutral (pI value of 5.5 to 8.5) and basic (pI value of higher than 8.5) regions (produced by Biologica Co.) were also used. Information on 4 peptides is shown in the following Table 1.

TABLE 1

| Peptide name | Sequence | Amino acid residues | Molecular weight | Isoelectric point (PI value) | SEQ ID NO: |
|---|---|---|---|---|---|
| ACTH | SYSMEHFRW GKPVGKKRR PVKVYP | 24 | 2933 | 10.6 | 3 |
| Factor XIII | AVPPNNSNA AEDDLPTVE LQGVVPR | 25 | 2602 | 3.9 | 4 |
| Fibrinogen α | DEAGSEADH EGTHSTKRG HAKSRPV | 25 | 2659 | 6.3 | 5 |
| ITIH4 | NVHSAGAAG SRMNFRPGV LSS | 21 | 2115 | 12.0 | 6 |

(3-2) Detection of Binding and Dissociation of ACTH-Binding Molecule and ACTH Peptide NeutrAvidin (SIGMA) was dissolved in 0.5×TBS to the final concentration of 0.1 µM to prepare a NeutrAvidin solution (0.1 µM). Three ACTH-binding molecules obtained in Example 1 were respectively dissolved in pure water to obtain solutions at 50 µM which were then further diluted 100-fold to prepare the respective ACTH-binding molecule solutions (0.5 µM). Freeze-dried powder of the above four peptides was respectively dissolved in 0.5×TBS to the final concentration of 17 µM to prepare the respective peptide solutions (17 µM).

A silicon nitride chip preliminarily modified with biotin (produced by Konica Minolta Opto Co., Ltd.) was mounted on an intermolecular interaction measuring device MI-Affinity (produced by Konica Minolta Opto Co., Ltd.) and flow paths on the chip were substituted with 0.5×TBS. The NeutrAvidin solution, the ACTH-binding molecule solution and the peptide solution were then injected respectively at 100 µL in this order to the flow paths. The NeutrAvidin solution was injected at the elapsed time of 0 sec, the ACTH-binding molecule solution at 1800 sec and the peptide solution at 3600 sec. Time course of the wavelength shift amount (nm) was observed by measurements according to RIfS. The resulting wavelength shift amount was plotted on coordinates with the elapsed time (sec) on the X axis and the wavelength shift amount (nm) on the Y axis.

Figure 3A:
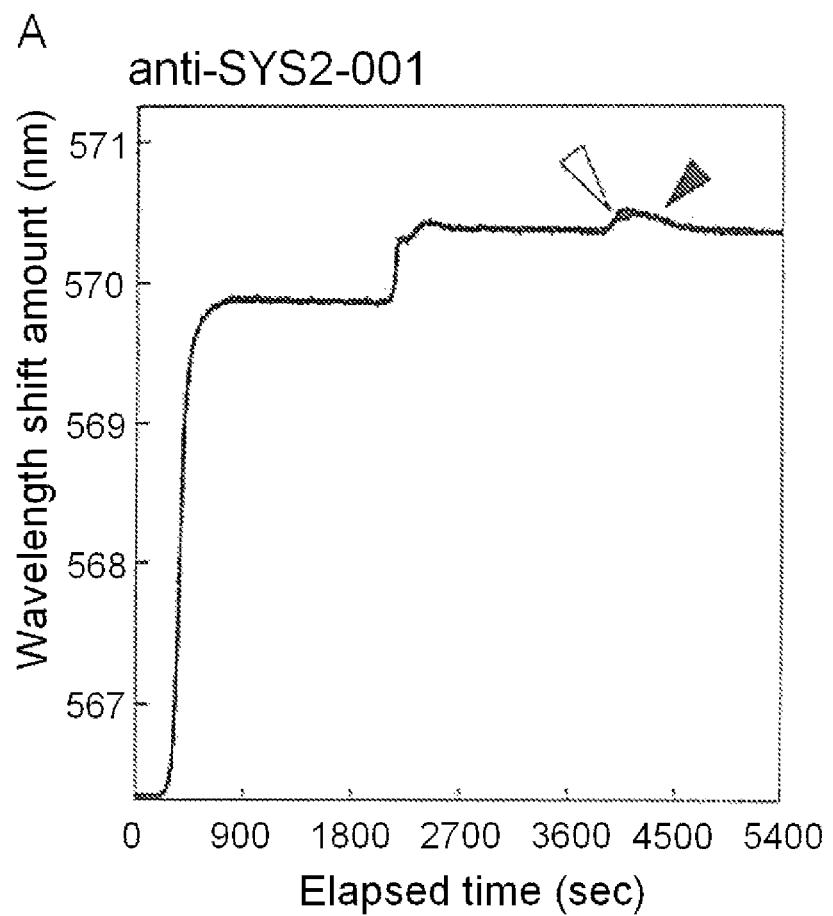
FIG. 3A, 3B and 3C are graphs obtained by measuring the interaction between an ACTH peptide and an ACTH-binding molecule of the present invention determined by reflectometric interference spectroscopy (RIfS) and plotting the obtained wavelength shift amounts on coordinates with the elapsed time on the X axis and the wavelength shift amount on the Y axis.
Figure 3B:
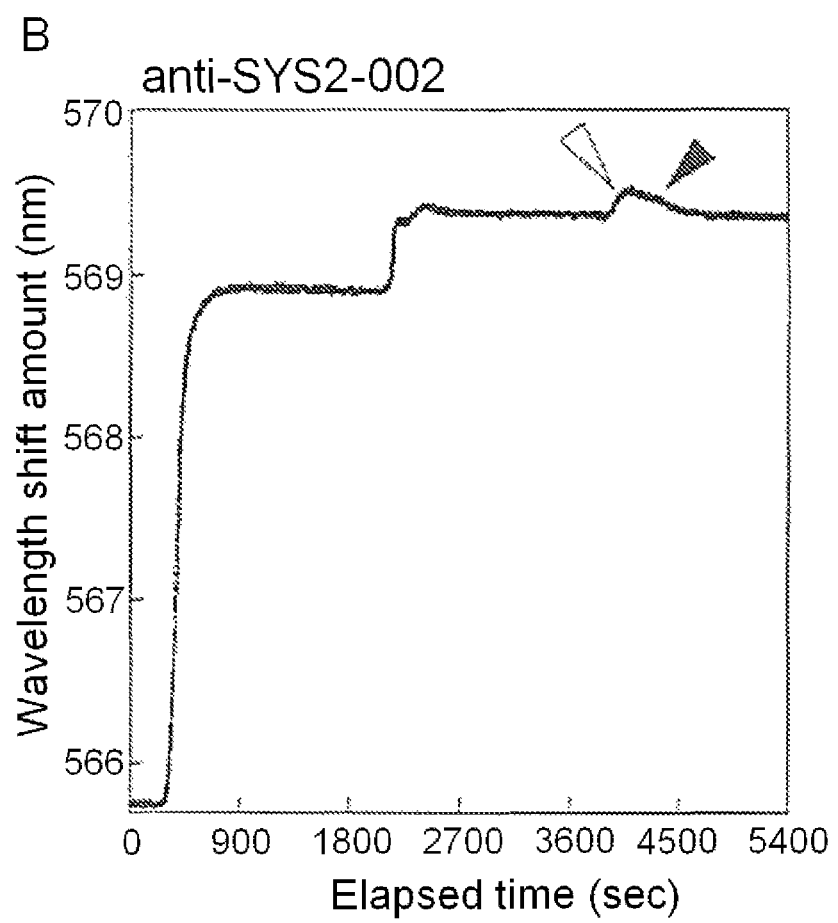
Figure 3C:
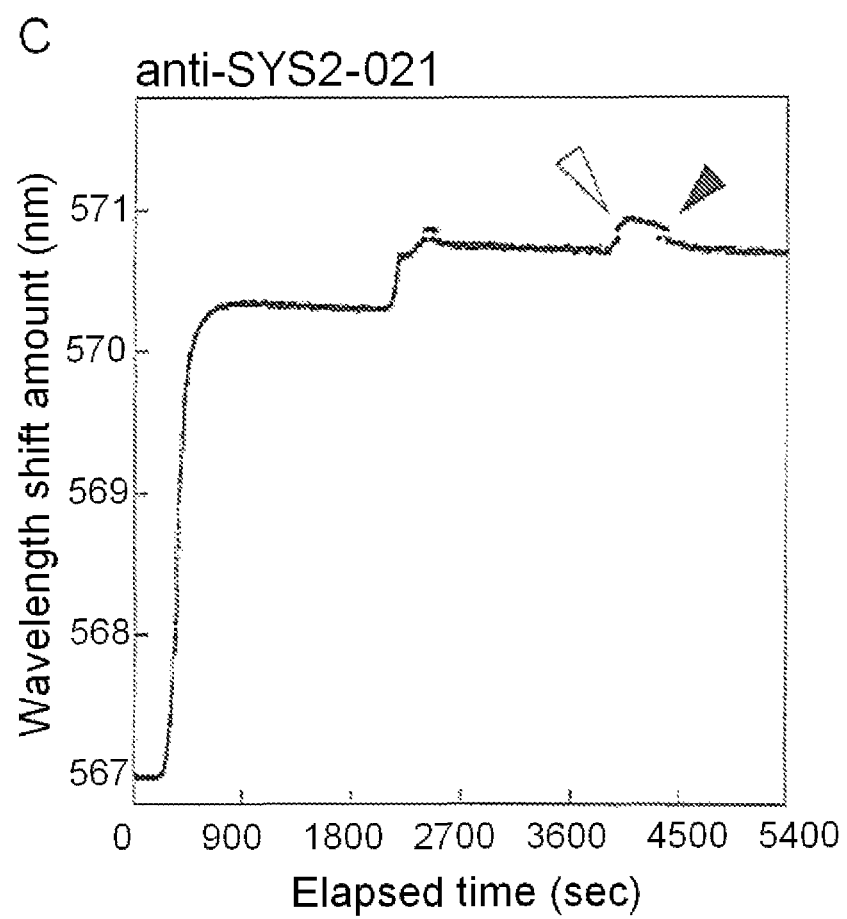
Figure 4:
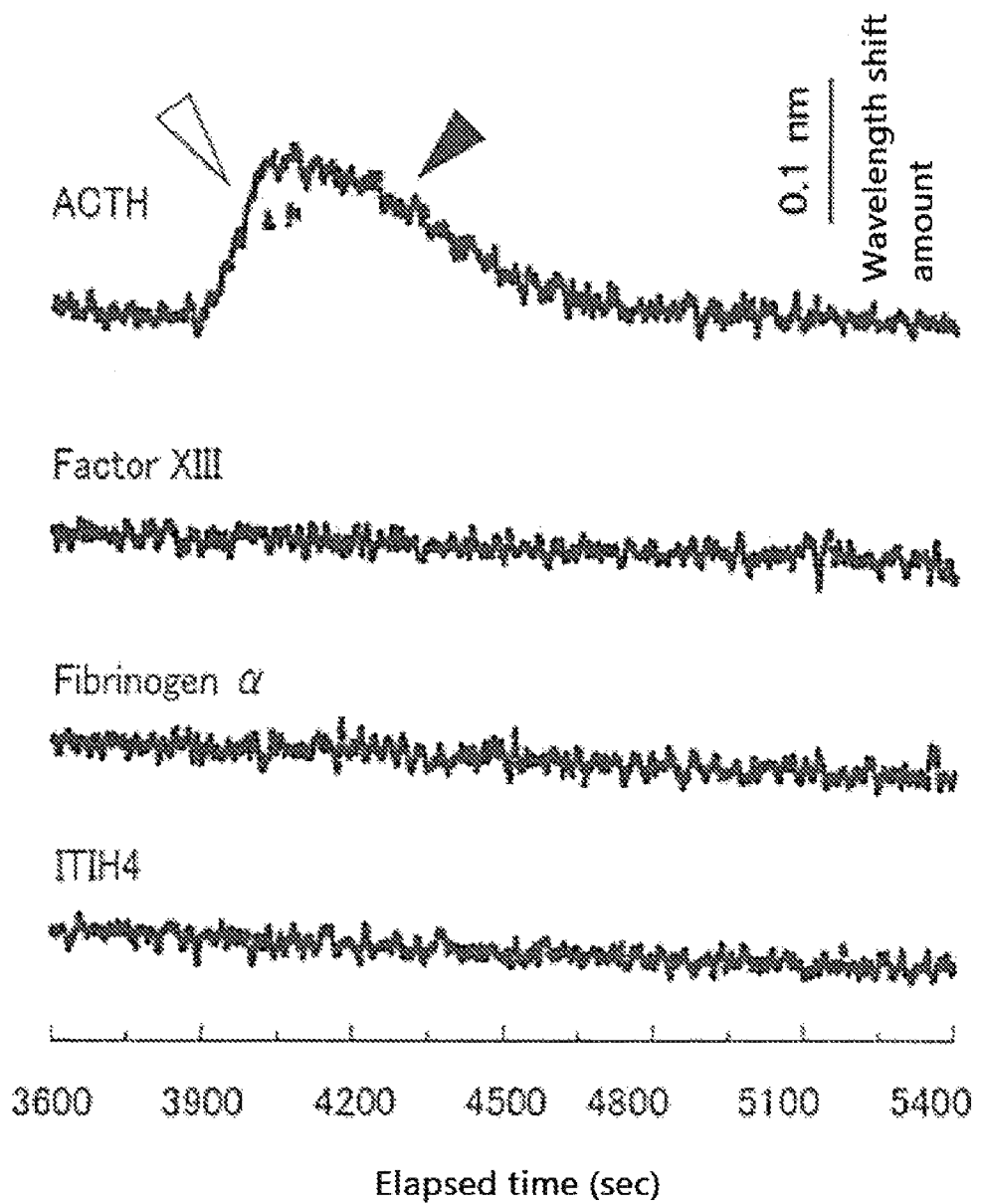
FIG. 4 is a graph showing variation in the wavelength shift amount after addition of four different peptide solutions.

Among the obtained graphs (hereinafter referred to as "sensorgrams"), the one obtained when the ACTH peptide solution was used as the peptide solution is shown in FIGS. 3A, 3B and 3C. Variation in the wavelength shift amount for anti-SYS2-001 after addition of four peptide solutions (i.e., after the elapsed time of 3600 sec) is shown in FIG. 4. In FIGS. 3A, 3B, 3C and 4, the peak indicative of binding of the ACTH peptide to the ACTH-binding molecule is marked with ∇ and the peak indicative of dissociation thereof is marked with ▼.

According to FIGS. 3A, 3B and 3C, all sensorgrams showed binding of NeutrAvidin to the biotin-modified SiN chip from 0 sec to 900 sec and binding of the ACTH-binding molecule to NeutrAvidin from 1800 sec to 2700 sec. When the ACTH peptide was injected at 3600 sec, a peak was observed which indicated binding and dissociation between the ACTH peptide and the ACTH-binding molecule. Thus it is found that ACTH could be detected by RIfS measurements using chips to which 3 ACTH-binding molecules were immobilized. Although noise was generated in the sensorgram of anti-SYS2-021 during measurement, binding and dissociation peaks with ACTH were observed, and thus the result showing detection of ACTH is not affected.

According to FIG. 4, it is found that the peaks of binding and dissociation between a peptide and an ACTH-binding molecule were only observed for ACTH and other peptides did not allow observation of such peaks. Thus it shows that the ACTH-binding molecules of the present invention specifically bind to the ACTH peptide.

Example 4

Study on Specificity of Binding between ACTH-Binding Molecule and Target Peptide Utilizing Competitive Inhibition By using the ITIH4 peptide which has similar molecular weight and isoelectric point as the ACTH peptide was used as a competitive inhibitor to study the specificity of the ACTH-binding molecule of the present invention towards a target peptide.

(4-1) Preparation of Samples

The samples for measurements, i.e., sample solutions E, F and G were prepared as follows. The sample solution E was obtained by dissolving the ACTH-binding molecule (anti-SYS2-002) and the TMR-ACTH peptide in 0.5×TBS to the final concentration of 800 nM, respectively. The sample solution F was obtained by dissolving the TMR-ACTH peptide in 0.5×TBS to the final concentration of 800 nM. The sample solution G was obtained by dissolving the ITIH4 peptide in 0.5×TBS to the final concentration of 1,000 μM.

(4-2) Measurement of Samples

Figure 5:
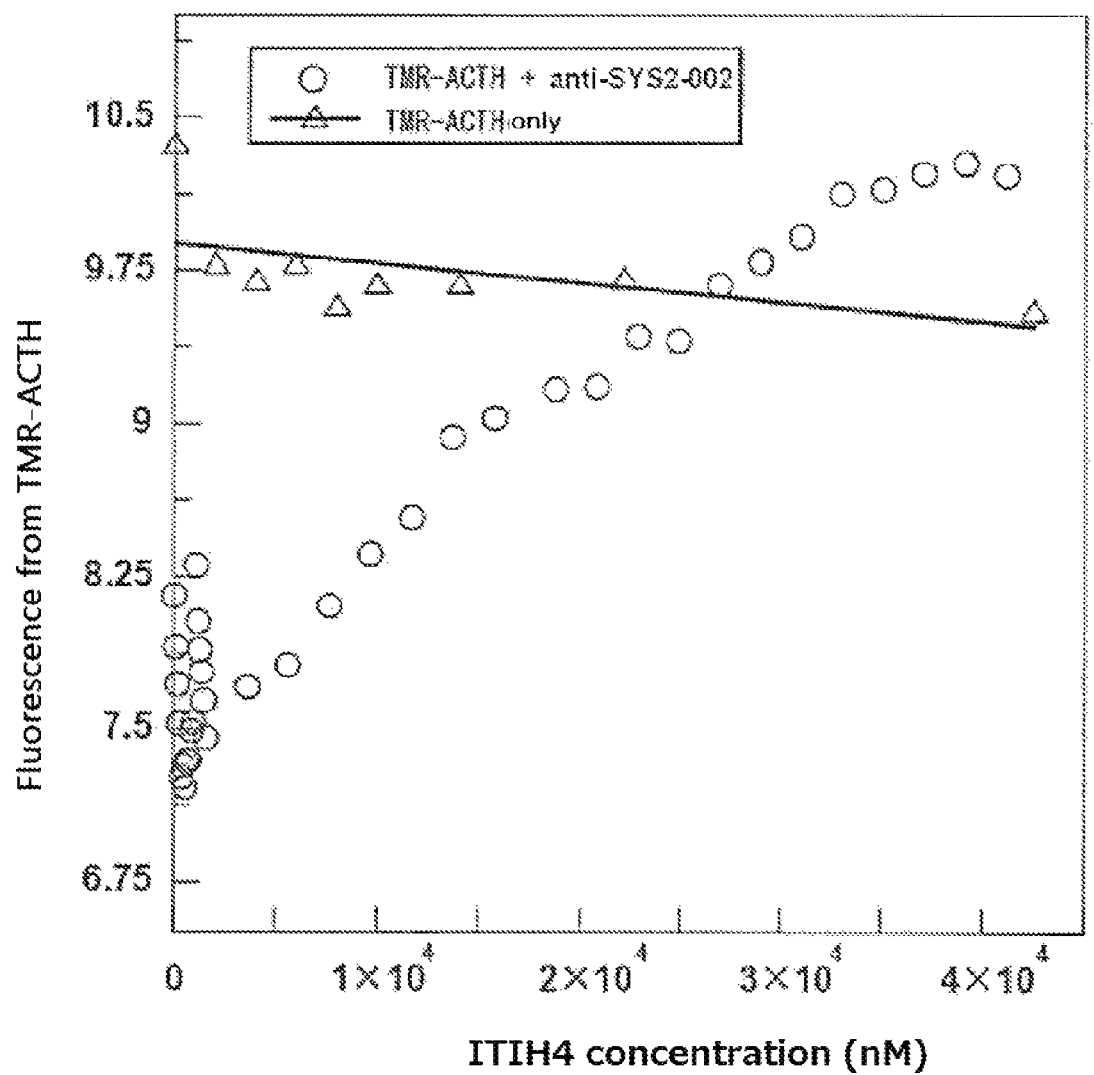
FIG. 5 is a graph obtained by plotting the fluorescence intensity measured for a sample solution containing an ACTH peptide and an ACTH-binding molecule of the present invention to which a ITIH4 peptide is added on coordinates with the concentration of the ITIH4 peptide on the X axis and the fluorescence intensity on the Y axis.

The sample solution E was measured for the fluorescence intensity at an excitation wavelength of 540 nm and fluorescence wavelength of 580 nm on Hitachi Fluorescence Spectrophotometer F-7000 (FL) (Hitachi High-Technologies Corporation). After the measurement, a small amount of the sample solution G was added to the sample solution E and thoroughly mixed to measure the fluorescence intensity. The sample solution G was further added to the mixed solution and the fluorescence intensity was measured again. This procedure was repeated and the obtained fluorescence intensity was plotted on coordinates with the concentration of the ITIH4 peptide on the X axis the fluorescence intensity on the Y axis. The sample solution F was subjected to similar procedures and the fluorescence intensity was plotted on the coordinates. The obtained graph is shown in FIG. 5.

Figure 6:
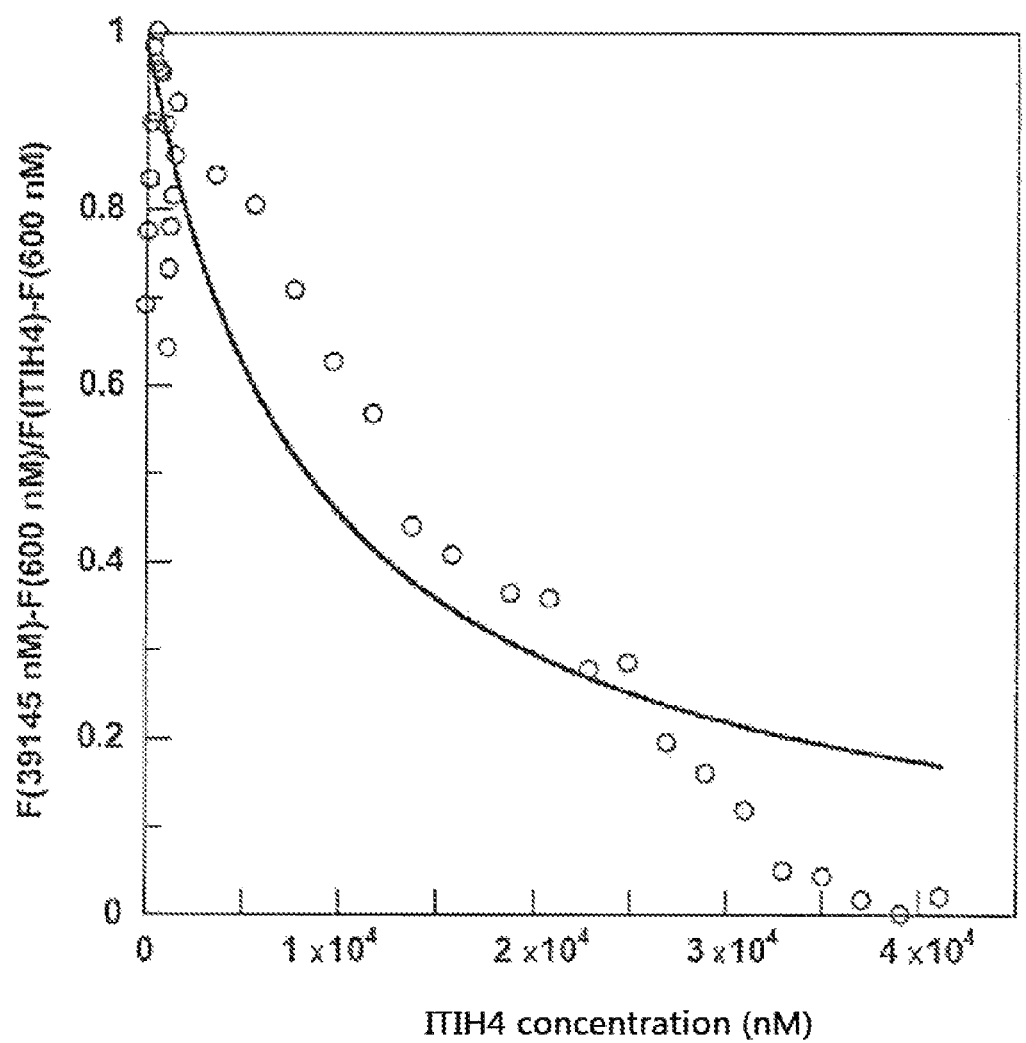
FIG. 6 is a graph obtained by normalizing the fluorescence intensity measured for a sample solution containing an ACTH peptide and an ACTH-binding molecule of the present invention to which a ITIH4 peptide is added and plotting the thus obtained data on coordinates with the concentration of the ITIH4 peptide on the X axis and the normalized fluorescence intensity on the Y axis.

The fluorescence intensity obtained from the measurement of the sample solution E was normalized and the data was plotted on coordinates with the concentration of the ITIH4 peptide on the X axis and the normalized fluorescence intensity on the Y axis. Curve fitting of the obtained graph to the following formula (II) by KaleidaGraph (Hulinks Inc.) was carried out for analysis. The analysis result is shown in FIG. 6.

$$Y = Ki \times [TMR\text{-}ACTH]Kd]/[X + \{Ki \times (Kd + [TMR\text{-}ACTH])/Kd\}]$$ Formula (II)

(wherein in the formula (II), Ki represents the $K_D$ value for binding of the ITIH4 peptide to the ACTH-binding molecule; and Kd represents the $K_D$ value for binding of the ACTH peptide to the ACTH-binding molecule).

According to FIG. 5, quenching of fluorescence of binding of the TMR-ACTH to the ACTH-binding molecule observed in Example 2 (FIG. 1) was canceled by addition of the ITIH4 peptide. In the absence of the ACTH-binding molecule, quenching of fluorescence was not canceled. Thus it is considered that variation (cancellation of quenching) in fluorescence due to addition of the ITIH4 peptide may occur due to interaction between the ITIH4 peptide and the ACTH-binding molecule. Namely, binding of the ITIH4 peptide to the ACTH-binding molecule caused release of the TMR-ACTH which had bound to the ACTH-binding molecule.

According to FIG. 6, Kd and Ki were respectively calculated as 1.3 nM and 850 nM. Using these results, the target specificity value S of the ACTH-binding molecule towards the ACTH peptide was calculated. The target specificity value S is the value obtained by division of the dissociation equilibrium constants of a target and a targeted substance (S=Ki/Kd). Thus a higher target specificity value S indicates higher specificity towards a target peptide.

The target specificity value S of the ACTH-binding molecule (anti-SYS2-002) of the present invention was calculated as 650. Thus it is found that the ACTH-binding molecule of the present invention can discriminate the ITIH4 peptide having the length (molecular weight) and isoelectric point respectively 72% and 89% homologous to the ACTH peptide with the specificity of the S value of 650. With regard to the target specificity, the report by SUSAN E. W. et al. (RNA, vol. 14, p. 1037-1047, 2008) is referred for comparison between the ACTH-binding molecule of the present invention and a conventional aptamer. Thus, the anti-p65 aptamer by SUSAN E. W. et al. can discriminate a protein (p50) having the length (molecular weight) and isoelectric point respectively 85% and 91% homologous to the target with the specificity of the S value of only 99. Therefore it is apparent that the ACTH-binding molecule of the present invention has higher target specificity than conventional aptamers.

Example 5

Detection of ACTH in Samples Containing Serum by RIfS Measurement (5-1) Preparation of Sample Solution A preliminarily prepared ACTH peptide solution (5 μL, 1.36 mM (4 mg/mL)), serum from a healthy subject (4 μL) and a ST buffer (10 mM Tris-HCl (pH 7.4), 100 mM NaCl) (391 μL) were mixed to prepare a serum sample containing the ACTH peptide. A serum sample without ACTH peptide was prepared by using pure water (5 μL) instead of the ACTH peptide solution.

(5-2) Detection of ACTH peptide in Serum sample by RIfS measurement

Figure 7:
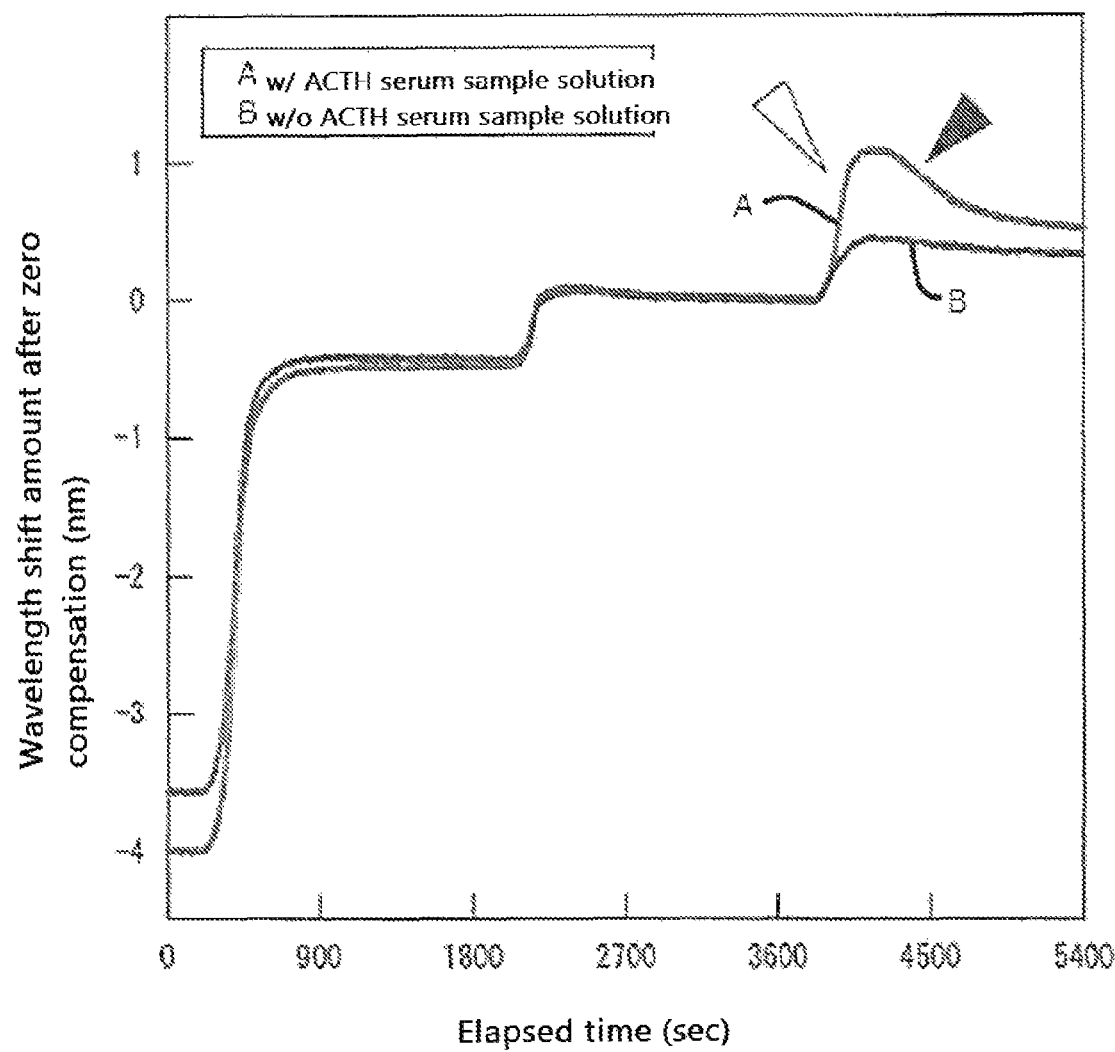
FIG. 7 is a graph obtained by measuring the interaction between an ACTH peptide in a serum sample and an ACTH-binding molecule by RIfS and plotting the obtained wavelength shift amount on coordinates with the elapsed time on the X axis and the wavelength shift amount on the Y axis.

In the same manner as Example 3, a silicon nitride chip preliminarily modified with biotin (produced by Konica Minolta Opto Co., Ltd.) was mounted on an intermolecular interaction measuring device MI-Affinity (produced by Konica Minolta Opto Co., Ltd.) and flow paths on the chip were substituted with 0.5×TBS. The NeutrAvidin solution (0.1 μM), the ACTH-binding molecule solution (0.5 μM) and the serum sample were injected respectively at 100 μL in this order to the flow paths. The NeutrAvidin solution was injected at the elapsed time of 0 sec, the ACTH-binding molecule solution at 1800 sec and the serum sample at 3600 sec. Time course of the wavelength shift amount (nm) was observed by measurements according to RIfS. FIG. 7 shows the sensorgram obtained by zero compensation of the obtained wavelength shift amount with the wavelength shift amount at 3600 sec. In FIG. 7, the peak indicative of binding of the ACTH peptide to the ACTH-binding molecule is marked with ▽ and the peak indicative of dissociation thereof is marked with ▼.

FIG. 7 shows, as similar to Example 3, the binding of the ACTH-binding molecule to the chip and, only when the serum sample containing the ACTH peptide was used, subsequent binding of the ACTH peptide to the ACTH-binding molecule (▽ in FIG. 7) and dissociation thereof (▼ in FIG. 7) was observed. Thus it is found that the ACTH-binding molecule of the present invention allows detection of ACTH peptides even in samples containing contaminants such as serum.

What is claimed is:

1. An andrenocorticotropic hormone-binding molecule comprising a nucleic acid sequence having a modified base represented by any one of (a), (b) and (c):

(a) $X_1TTX_2X_3TX_3TX_4GX_4GAX_5TX_2X_1TX_6C$ (b) $AX_5X_7GTX_2X_6CX_3TX_4GTX_2X_3TX_6CTX_8$ (c) $X_6CTX_2AX_5TX_2X_9AX_1TX_7GX_6CAX_5TX_2$ wherein $X_1$ to $X_9$ respectively represent modified bases represented by the following formulae, wherein P represents a phosphate group:

$X_1$

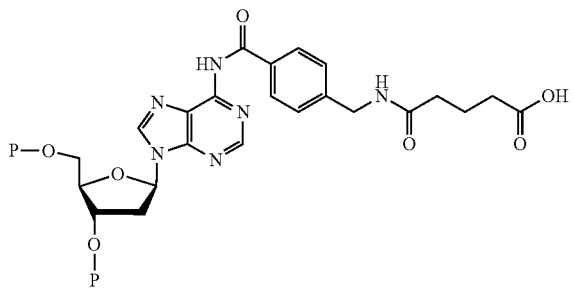

$X_2$

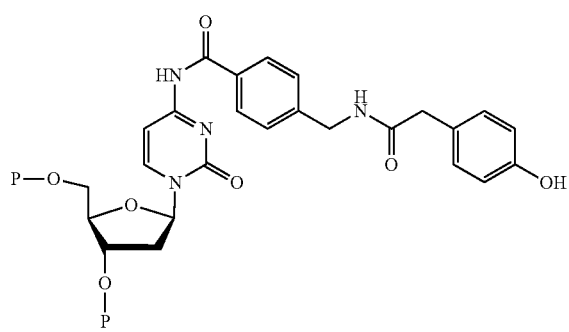

$X_3$

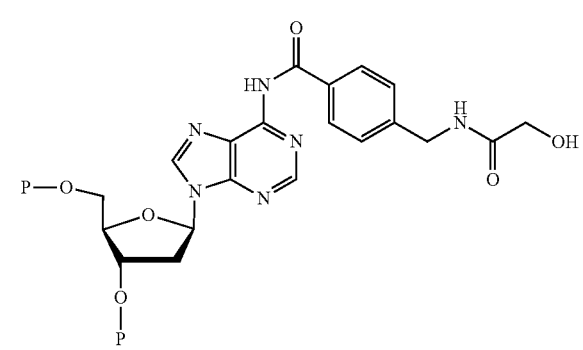

$X_4$

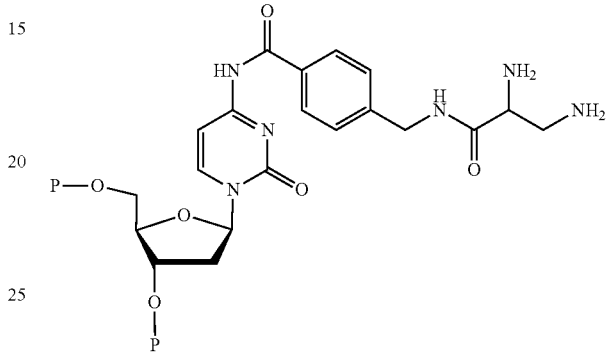

$X_5$

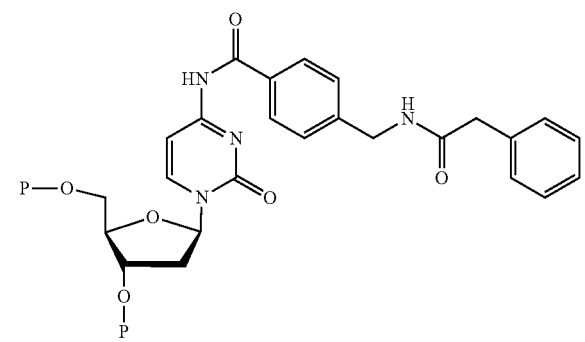

$X_6$

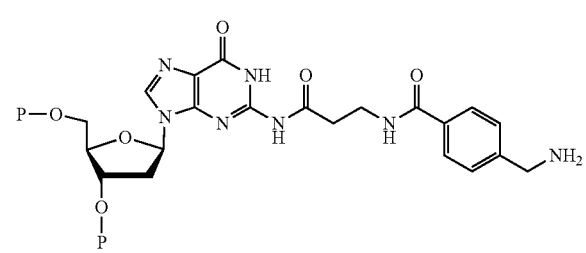

$X_7$

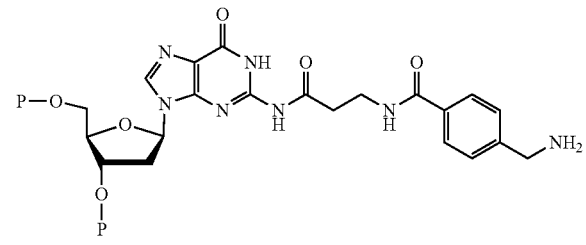

-continued

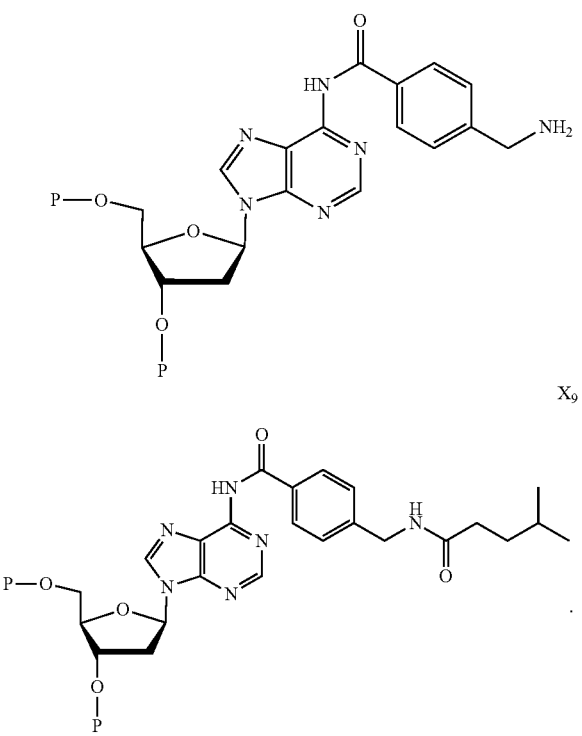

2. The andrenocorticotropic hormone-binding molecule according to claim 1, further comprising an additional sequence.

3. The andrenocorticotropic hormone-binding molecule according to claim 1, further comprising a linker.

4. The andrenocorticotropic hormone-binding molecule according to claim 3, wherein the linker is at least one selected from a linear synthetic polymer and a linear natural polymer.

5. The andrenocorticotropic hormone-binding molecule according to claim 4, wherein the linear synthetic polymer is at least one selected from polyethylene glycols, polyvinylpyrrolidones and polyvinylacetamides.

6. The andrenocorticotropic hormone-binding molecule according to claim 4, wherein the linear natural polymer is at least one selected from nucleic acids, polysaccharides and proteins.

7. A carrier linked to the andrenocorticotropic hormone-binding molecule according to claim 1.

8. A reagent for andrenocorticotropic hormone detection comprising the andrenocorticotropic hormone-binding molecule according to claim 1.

9. A method for detecting andrenocorticotropic hormone comprising the steps of:
   mixing a sample with the andrenocorticotropic hormone-binding molecule according to claim 1; and
   analyzing binding of the andrenocorticotropic hormone-binding molecule to andrenocorticotropic hormone in the mixture obtained in the previous step, thereby detecting andrenocorticotropic hormone.

10. The method according to claim 9, wherein the analysis of binding of the andrenocorticotropic hormone-binding molecule to andrenocorticotropic hormone is carried out by irradiating the mixture with light to obtain optical information.

11. The method according to claim 10, wherein the optical information is a wavelength of reflected light, a fluorescence intensity or an absorbance.

12. A method for purifying andrenocorticotropic hormone comprising the steps of:
   mixing a sample with the carrier according to claim 7; and
   purifying the andrenocorticotropic hormone from the mixture obtained in the previous step as a complex of the andrenocorticotropic hormone-binding molecule linked to the carrier and the andrenocorticotropic hormone.

13. The method according to claim 9, wherein the sample is a biological sample.

14. The method according to claim 13, wherein the biological sample is blood, plasma, serum or body fluid.

* * * * *

SEQUENCE LISTING

<160> NUMBER OF SEQ ID NOS: 6

<210> SEQ ID NO 1
<211> LENGTH: 35
<212> TYPE: DNA
<213> ORGANISM: Artificial Sequence
<220> FEATURE:
<223> OTHER INFORMATION: Synthetic polynucleotide sequence

<400> SEQUENCE: 1
gaaggtgaag gtcggctgaa gcattagacc taagc                              35

<210> SEQ ID NO 2
<211> LENGTH: 33
<212> TYPE: DNA
<213> ORGANISM: Artificial Sequence
<220> FEATURE:
<223> OTHER INFORMATION: Synthetic polynucleotide sequence

<400> SEQUENCE: 2
gcttaggtct aatgcaccat catcaccatc ttc                                33

<210> SEQ ID NO 3
<211> LENGTH: 24
<212> TYPE: PRT
<213> ORGANISM: Homo sapiens

<400> SEQUENCE: 3

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 4
<211> LENGTH: 25
<212> TYPE: PRT
<213> ORGANISM: Homo sapiens

<400> SEQUENCE: 4

Ala Val Pro Pro Asn Asn Ser Asn Ala Ala Glu Asp Asp Leu Pro Thr
1               5                   10                  15

Val Glu Leu Gln Gly Val Val Pro Arg
            20                  25

<210> SEQ ID NO 5
<211> LENGTH: 25
<212> TYPE: PRT
<213> ORGANISM: Homo sapiens

<400> SEQUENCE: 5

Asp Glu Ala Gly Ser Glu Ala Asp His Glu Gly Thr His Ser Thr Lys
1               5                   10                  15

Arg Gly His Ala Lys Ser Arg Pro Val
            20                  25

<210> SEQ ID NO 6
<211> LENGTH: 21
<212> TYPE: PRT
<213> ORGANISM: Homo sapiens

<400> SEQUENCE: 6

Asn Val His Ser Ala Gly Ala Ala Gly Ser Arg Met Asn Phe Arg Pro
1               5                   10                  15
Gly Val Leu Ser Ser
            20